United States Patent [19]

Gordon

[11] Patent Number: 4,813,399
[45] Date of Patent: Mar. 21, 1989

[54] PROCESS FOR THE TREATMENT OF NEUROLOGICAL OR NEUROMUSCULAR DISEASES AND DEVELOPMENT

[76] Inventor: Robert T. Gordon, 4936 W. Estes, Skokie, Ill. 60077

[21] Appl. No.: 886,616

[22] Filed: Jul. 18, 1986

[51] Int. Cl.⁴ ............................................. A61N 1/42
[52] U.S. Cl. ..................................... 600/12; 128/654; 424/9
[58] Field of Search ..................... 128/1.3–1.5, 128/1.1, 1 R, 804, 399, 653–654; 424/1.1, 1.5, 9; 422/20–22

[56] References Cited

U.S. PATENT DOCUMENTS

| | | | |
|---|---|---|---|
| 4,106,488 | 8/1978 | Gordon | 128/1.1 X |
| 4,136,683 | 1/1979 | Gordon | 128/1.3 X |
| 4,303,636 | 12/1981 | Gordon | 424/1 |
| 4,359,453 | 11/1982 | Gordon | 424/1 |
| 4,545,368 | 10/1985 | Rand et al. | 128/1.5 X |
| 4,569,836 | 2/1986 | Gordon | 128/804 X |
| 4,590,922 | 5/1986 | Gordon | 128/1.3 |
| 4,622,952 | 11/1986 | Gordon | 128/1.3 |
| 4,622,953 | 11/1986 | Gordon | 128/1.3 |
| 4,662,359 | 5/1987 | Gordon | 128/1.1 |
| 4,665,898 | 5/1987 | Costa et al. | 128/1.3 |
| 4,735,796 | 4/1988 | Gordon | 128/1.3 X |

Primary Examiner—Kyle L. Howell
Assistant Examiner—Angela D. Sykes
Attorney, Agent, or Firm—Banner, Birch, McKie & Beckett

[57] ABSTRACT

The present invention describes a method for the treatment of neurological diseases and development and neuromuscular diseases and development with diagnostic applications to optimize the treatment modalities. The process involves the use of magnetic or electric dipoles which are present, capable of being induced or introduced into neurological or neuromuscular tissue and are capable of being activated by an external alternating electromagnetic field. The cells in the neurological or neuromuscular tissue may consist of neurons (central or peripheral) and supporting cells i.e. glial cells, oligodendrocytes, etc. The activation of these magnetic or electric dipole particles allows modulation and control of neuronal and supporting cell activity.

61 Claims, 1 Drawing Sheet

ANALOGOUS ELECTRICAL CURRENT

NEUROMUSCULAR JUNCTION

4,813,399

PROCESS FOR THE TREATMENT OF NEUROLOGICAL OR NEUROMUSCULAR DISEASES AND DEVELOPMENT

INTRODUCTION

The treatment of neurological or neuromuscular disorders currently is limited to chemotherapy and various surgical approaches. The use of drugs is limited because of side-effects and the blood-brain barrier, Various drugs are used to affect neurotransmission to the extent that even neurotransmitters are used. The ability to control neurological or neuromuscular disorders with drugs is very limited and in many cases the mechanisms are not completely understood. In addition the ability to control the development and regeneration of nervous tissues as well as other tissues has not been achieved prior to this present invention.

BACKGROUND OF THE INVENTION

Diseases which affect the neurological system are multiple and consist of inflammatory lesions, conduction problems, and neurotransmission disorders. Different processes affect central nervous tissue vs. peripheral nervous tissue, myelinated nerve fibers vs. unmyelinated nerve fibers, and neurons themselves vs. glial cells and supporting cells. Most neurological diseases can only be very minimally treated because of the inaccessability of nervous tissue. Examples include amyotrophic lateral sclerosis, Alzheimer's disease, multiple sclerosis, Parkinson's disease, spinal cord problems i.e. diabetic neuropathy and retropathy, etc. Disorders of embryogenesis and development of neurological tissue as well as other tissues occur quite frequently and until the present invention there are very few methods of attempting to control this process. Developmental disorders are characterized by spinal cord malformations (i.e. spina-bifida, etc.) and cerebral malformations (hydrocephalous, etc.). Malignancies of the neurological system are also at present difficult to manage and extremely common in the developmental stages.

The present invention seeks to overcome this problem by modifying the intracellular environment in the neural and supporting cells to control the disease process.

OBJECT OF THE INVENTION

The present invention seeks to control the function of neurological tissue by the use of intracellular particles which are present, capable of being induced or introduced and the use of an alternating electromagnetic field to affect these particles and consequently the neurological tissue. Though the introduction of intracellular energy the function of the neuron as well as the conduction of the impulse can be controlled. A constant magnetic field can be used to impart a dipole to the particles prior to treatment with the alternating electromagnetic field to enhance the effect. In addition the constant magnetic field can be used to modify the behavior of the neural cells and to modulate the disease process or conduction mechanism.

DETAILED DESCRIPTION OF THE INVENTION

The use of particles to alter the energy level in the cell by the absoption of electromagnetic energy by the particle has been disclosed in the Applicant's U.S. Pat. Nos. 4,106,488; 4,136,683; 4,303,636; and 4,359,453. The present invention seeks to use particles to affect the absorption of energy by the cell itself and in particular by neural cells in the tissue. The implementation of this present treatment method in part utilizes inventive aspects which are the subject of other applications for U.S. Letters Patent by the same inventor as recited hereinafter. For example, a fuller understanding of the technology underlying the Gordon treatment reveals the operation of subtle mechanisms which can themselves become a contributing factor in the course of treatment and are incorporated herein by reference. The selection of particle compositions for use in this present invention as disclosed in the applicant's above described U.S. Patents and as disclosed in copending and commonly assigned applications. Ser. Nos. 418,298; 464,870 including Ser. No. 522,941, including Ser. NO. 535,390, now U.S. Pat. No. 4,662,359; and 561,811 as well as application Ser. No. 627,536 of the same inventor, are incorporated herein by reference.

Below several MHz the transmission of energy directly to the cell by an external alternating electromagnetic field is affected by the characteristics of the cell membrane. The charge accumulation on the membrane from intracellular and extracellular fluids accounts for the dielectric polarization of the membrane. The intracellular and extracellular electrolyte solution accounts for the conductance.

In the prior Gordon U.S. Pat. Nos. 4,303,636; 4,106,488; and 4,359,453, a high frequency magnetic field is employed to have a direct effect on the particles so that diseased cells can be killed by thermal effects due to hysteresis loss from the particles themselves when the field is relaxed. The particles of the present invention are utilized to alter the behavior of neuronal cells and supporting cells.

Through the introduction of particles in the nerve cells the intracellular conductivity can be altered as well as the charge accumulation on the cell membrane. The alteration in cell membrane characteristics enables the delivery of energy intracellularly at a lower frequency due to the effect of the charge accumulation on the cell membrane and the increased conductivity of the nerve cell allows more energy to be delivered and a better coupling at the given frequency.

Figure 1:
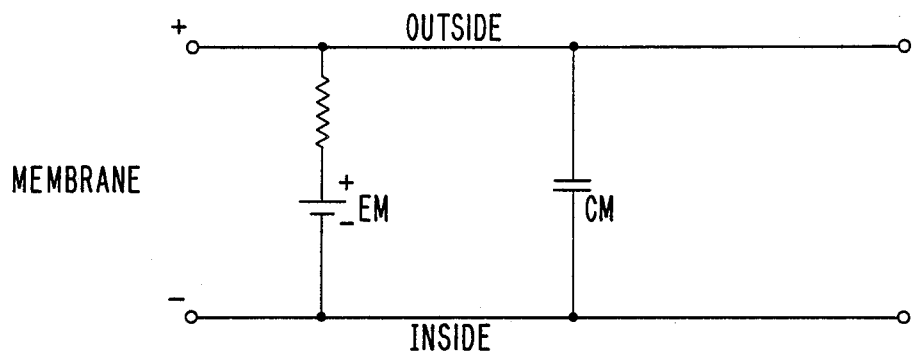

Mechanical, chemical, thermal stimuli as well as electrical can activate a nerve. Actiation consists of initiation of an action potential with an alteration of ion permeability and the corresponding ion flexes. An analogous electrical circuit is described in FIG. 1. Obviously any change inside the cell will affect membrane polarization and conduction.

Figure 2:
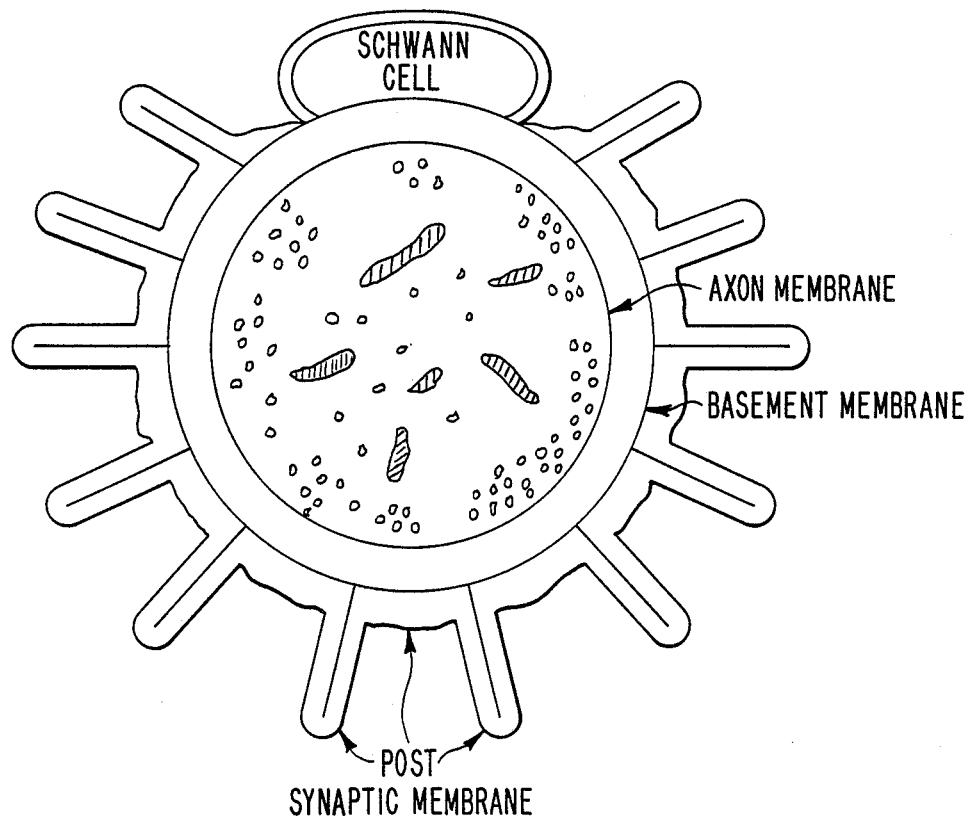

Synapses occur as connections between nerves and between nerves and other tissues. An example is the neuromuscular junction where the nerve ending is connected to the end plate of themuscle fiber. The nerve terminal is full of synaptic vesicles and mitochondria. This is illustrated in FIG. 2.

The neurotransmitters are often released at nerve endings or at synapses. Examples are acetylcholine or nor-epinephrine.

Iron is taken up quite well by certain areas of the brain. In certain pathological conditions increased or different accumulations of iron can occur. The blood brain barrier prevents the passage of most proteins into the brain. However the capillaries in the brain have demonstrated transferrin receptors for the uptake of iron. These are the only capillary receptors for transferrin in the body. Therefore iron uptake in the brain occurs by endocytosis via a receptor mediated mechanism. Iron is demonstrated in oligodendrocytes, glial cells and neurons. In addition active neurons have an inherent magnetic field secondary to their electric current. These magnetic fields can be monitored.

Neurons contain receptors. Transferrin receptors have been demonstrated on axons and cendrites. The ligand reaction with the receptor changes the membrane potential and ionic conductance which changes characteristics of nerves and causes transmitter release. An electric field can also affect transmitter release.

The uptake of iron in the brain can be modulated by chemical means. Chloroquin which is lysosonotropic can decrease the uptake by neuronal and glial cells. This uptake can also be decreased by ammonium chloride or methylamine. Iron accumulation in the brain is associated with neuromelanin, ceroid-lipofuscin and Hallervorden-Spatz syndrome.

The transport of iron particles and other particles in myelinated and unmyelinated fibers depends on the particle size and composition. Neurons take up iron particles by endocytosis. In unmyellinated nerves iron-dextran particles are transpoted along the unmyelinated pathways to the substantia nigra. After injection Fe-dextran is taken up by axons and transported retrograde to cell bodies. (No toxicity from iron particles in ganglion cell bodies of neuron).

Transport of the particles is extremely dependent on cell type and particle size, composition and conformation. In myelinated nerves iron-dextran is transported to the cell bodies in 2–3 weeks at a rate of 1–2 mm/day. However horse-radish peroxidase (HRP) is transported to the cell bodies in 20 hrs. at a rate of ;b 2–3 mm/hour. Therefore different particles can be used to produce the effect in different areas. The iron dextran is longer than HRP and achieves cell body localization at a later time.

Most ganglia cells (cell bodies) will demonstrate iron after the axons are exposed to particles. In axons the iron dextran can cause swelling of myelin layers. The particles can embed in the myelin and react with it to decrease transport. However in the present invention the association of the particles with the myelin allows an affect to the myelin layers and the conduction in the axon. This is especially useful in diseases affecting the myelination of nerves.

Oligodendrocytes have endogenous iron and avidly take up Fe-dextran particles. This allows the ability to affect the function of the supporting glial cells as well.

Therefore the nerves do take up and transport iron particles. The present invention provides the ability to effect cells and metabolism in nerves and neurons. The particles can also be directed to the mitochondria of the axons and therefore affect the metabolic rate as well as the conduction of the nerves. The presence of these particles in the mitochondria at the nerve terminals in synapses or at neuromuscular junction allows for control of neurotransmitter release and also neuromuscular function.

Unmyelinated fibers label quickly with iron-dextran particles and travel via the nigrostriatal pathway to the thalamus and locus coeruleus pathway. This route canbe used to affect central portions of the brain with the present invention.

Retinal ganglion cells can be labeled by injection into the superior colliculus and the lateral geniculate nucelus. This allows for control of the visual pathways. The dopaminergic neurons of the substantia nigra after striatal injection can also be controlled. Different pathways also transport the particles at a different rate.

In certain circumstances unmyelinated fibers as in the nigrostratatal system transport faster than the myelinated visual system. This can be due to the interaction of the particles with the myelin. This allows for control of one pathway over another depending on the timing and type of particle utilized. The transport of iron-dextran is affected by the interaction of the particles with the myelin and the uptake by the glial cells which decreases central transport. In thinly myelinated pathways as in the striatum-thalamus and thalamus-nucleus reticulous thalami paths the transport of iron particles is faster due to the decrease in interaction with the myelin. The fastest path for iron-dextran particles is the unmyelinated paths i.e. dopaminergic nigro striatal pathway and thalamus-locus coeruleus noradrenergic path.

The process of the present invention involves the use of intracellular particles to modify and modulate neuronal and glial cell function. These particles may be introduced into the subject by intravenous, intraarterial, intralymphatic injection or injection into the cerebrospinal fluid. The paerticles may also be injected directly into the neurrological tissue or a specific pathway.

This process also applies to neurological tissue and other tissue during development to modify the developmental process. The expression of transferrin receptors for iron particles is extremely high during this phase.

The particles are of a ferromagnetic, paramagnetic, or diamagnetic nature and therefore capable of responding to an external alternating electromagnetic field. The particles, in general, are under 1 micron in size and in a colloidal-type suspension although for a direct injection they may be directly introduced.

In addition, any electric or magnetic dipole in the cell or capable of being induced in the cell may be utilized. A constant magnetic field can be used to induce these dipoles as well as enhance the effect of the external alternating electromagnetic field or dipoles or particles containing these dipoles which are present in the cell. This constant magnetic field can be used to help maximize particle uptake and absorption, and to help concentrate the particles in the desired area.

The choice of particle type, size and shape can be highly significant to effective treatment, particularly where subcellular localization or other subtle differentiations in metabolic activity, for example, are conveniently utilized to maximize particle uptake and absorption. Different particles are chosen depending on the desired pathway or ultimate area of nervous tissue which is desired to be affected as described above. Suitable particles and exemplifications of selection parameters are disclosed and examined in copending and commonly assigned Application Ser. No. 535,390, now U.S. Pat. No. 4,662,359, incorporated herein by reference.

The particle systems include metalloporphyrins, $Fe_2O_3$, metal-metalloporphyrins and particularly useful particle including both inorganic elements and compounds as well as metal containing organic compounds. Inorganic elements and compounds particularly well suited, owing to their favorable magnetic parameters, comprise elements such as dysprosium, erbium, europium, gadolinium, holmium, samarium, terbium, thulium, ytterbium or yttrium and compounds thereof such as dysprosium sulfate, erbium sulfate, europium oxide, europium sulfate, gadolinium oxide, gadolinium sulfate, holmium oxide, samarium sulfate, terbium oxide, terbium sulfate, thulium oxide, ytterbium sulfate, yttrium oxide, yttrium sulfate, yttrium ferrioxide ($Y_3Fe_5O_{12}$), yttrium aluminum oxide ($Y_3Al_5O_{12}$), other dimetallic compounds such as dysprosium-nickel, dysprosium-cobalt, gadolinium-iron, ytterbium-iron, cobalt-samarium, gadolinium-yttrium, and dysprosium-gallium, and actinide series elements and compounds thereof.

Metal containing-organic molecules useful for the application described above, comprise particles of iron-dextrans such as FeOOH-dextran complexes and other dextran metal complexes wherein the metal is selected from the group comprising cobalt, iron, zinc, chromium, nickel, gallium, platinum, manganese and rare earth metals such as dysprosium, erbium, europium, gadolinium, holmium, samarium, terbium, thulium, ytterbium and yttrium, other dimetallic compounds such as dysprosium-nickel, dysprosium-cobalt, gadolinium-iron, ytterbium-iron, cobalt-samarium, gadolinium-yttrium, and dysprosium-gallium and iron such as $Fe_2O_3$ particles, $Fe_3O_4$ particles and FeOOH particles and $Fe_2O_3$-dextran complexes, $Fe_3O_4$-dextran complexes, and FeOOH-dextran complexes, and actinide series elements and compounds, ferric ammonium citrate, and various iron transporting and chelating compounds such as enterochelin, transferrin, etallothionein, hydroxamates, phenolates, ferrichromes, desferri-ferrichromes, ferritin, ferric mycobactins, and iron-sulfur proteins such as ferredoxin and rubredoxin and transferrin as well as transferrin compounds and complexes.

Particularly appropriate metal-containing organic structures for use with the present invention are the porphyrins such as etioporphyrins, mesoporphyrins, uroporphyrins, coproprophyrins, protoporphyrins, and dicarboxylic acid containing porphyrins and substituted porphyrins such as tetraphenylporphyrin sulfonate (TPPS). Especially advantageous protoporphyrins comprise hematoporphyrins, chlorophylls, and cytochromes. In addition to the naturally occuring protoporphyrins which possess either iron or magnesium containing moieties, mixed-metal or di-metal hybrid porphyrins may also be prepared. For example, by substituting an alternative metal for the iron in hematoporphyrin, the advantages of the porphyrin moiety in terms of specificity of localization is retained while the unique magnetic properties of the new metal enhance the sensitivity of the substituted molecule. Suitable metals for purposes of substitution comprise cobalt, iron, manganese, zinc, chromium, gallium, nickel, platinum and rear earth series of metals such as dysprosium, erbium, europium, gadolinium holmium, samarium, terbium, thulium, ytterbium and ytterium, dimetallic compounds such as dysprosium-nickel, dysprosium-cobalt, gadolinium-iron, ytterbium-iron, cobalt-samarium, gadolinium-yttrium, dysprosium-gallium and actinide series elements and compounds thereof. The substituted porphyrins are then optionally reacted with dextran to form a metal-containing porphyrin dextran complex in particle form. Suitable porphyrin acceptors comprise any dicarboxylic acid containing porphyrin such as protoporphyrins (e.g. hematoporphyrins) and the like.

The substitution reaction is carried out in vitro by reacting the desired metal with the desired porphyrin in the presence of the enzyme ferrochelatase (E.C. 4.11.1.1). Reaction conditions as described by Jones and Jones (Biochem. J. 113:507–14, 1969) or Honeybourne, et al (FEBS Lett.: 98:207–10, 1979) are suitable.

Additional particle systems particularly suited to use in this present invention include $Fe_4O_4$-transferrin dextran, metal-transferrin (transition, rare-earth), metalloporphyrin-transferrin, antibody-ferritin-particles, antibody-ferritin-transferrin particles, antibody-transferrin particles, metal-porphyrin-metal complexes, metallothionein particles, and lectin particles. Useful particle systems for use in this present invention further comprise: Where particle=$Fe_3O_4$, transition metal, rear-earth metal, metalloporphyrin, etc. as well as ferromagnetic and paramagnetic particles.

One magnetic characteristic known to be temperature dependent is magnetic susceptibility. Magnetic susceptibility is measured by the ratio of the intensity of magnetization produced in a substance to the magnetizing force or intensity of the field to which it is subjected. This magnetic characteristic is routinely measured by magnetometer devices such as a vibrating magnetometer or a flux gate magnetometer. Therefore, by measuring the magnetic susceptibility of particles at various temperatures, it is quite simple to calibrate the magnetometer equipment so that when it measures the magnetic susceptibility of the particles a simple calibration will indicate the exact corresponding temperature of the particle.

By way of illustrating the increased magnetic susceptibility of some of the elements or compounds described above, the following table is provided:

| Element or Compound | Temp (K.) | Mag. Sus. ($10^6$ cgs) |
| --- | --- | --- |
| Iron Oxide (ref.) | 293 | +7,200 |
| Dysprosium Oxide | 287.2 | +89,600 |
| Dysprosium Sulfate Octahydrate | 291.2 | +92,760 |
| Erbium Oxide | 286 | +73,920 |
| Erbium Sulfate Octahydrate | 293 | +74,600 |
| Europium | 293 | +34,000 |
| Europium Oxide | 298 | +10,100 |
| Europium Sulfate | 293 | +25,730 |
| Holmium Oxide | 293 | +88,100 |
| Holmium Sulfate Octahydrate | 293 | +91,600 |
| Terbium | 273 | +146,000 |
| Terbium Oxide | 288.1 | +78,340 |
| Terbium Sulfate Octahydrates | 293 | +76,500 |
| Thulium | 291 | +25,500 |
| Thulium | 296.5 | +51,444 |
| Ytterbium Sulfide | 292 | +18,300 |

Thus, the enhanced magnetic characteristics displayed by the particles of the subject invention result in an increase in an electromagnetic field thereby increasing the overall sensitivity and control of the modalities for the improvement of the present invention techniques and for the resultant effects.

Magnetic susceptibility has also been used heretofore in connection with the treatment protocol as disclosed in U.S. Pat. No. 4,136,683 of the same inventor, where magnetic susceptibility measurements are correlated with temperature (an interdependent variable) in accomplishing the related induction heating step controllably. There is no recognition, however, that the values for magnetic susceptibility, independent of the induction heating step or the imposition of an electromagnetic field can be usefully correlated (to maximization of particle concentration with time to optimize treatment effectiveness, as demonstrated herein.

A further benefit is derived from the fact that some particle compositions comprise a ferromagnetic, paramagnetic, or diamagnetic component integrated into a cell or organelle specific molecular structure, thereby permitting efficient targeting and delivery of said particles to specific intracellular compartments such as mitochondria, chloroplasts, nuclei, vacuoles, and the like.

In addition, particle systems which are kept outside the neural cells may be utilized to alter membrane events and effect the frequency of response and the energy transmission of the diseased neuronal cells. In certain circumstances these particles may be utilized to stabilize the membrane of normal neuronal cells and decrease their response to a field at a given frequency.

A steady magnetic or electric field may be used to enhance the uptake of particles by the neuronal cells as well as enhancing the membrane and cytoplasmic alterations which occur and are fully disclosed and described in copending and commonly assigned Application Ser. No. 535,390, now U.S. Pat. No. 4,662,359, of the same inventor incorporated herein by reference. For example, the application of the localized static magnetic or electric field may occur concurrently with the application of an alternating, oscillating or pulsed electromagnetic field. That is to say, the localized static magnetic or electric field may be superimposed on the subject of interest while the alternating, oscillating or pulsed field is also being applied.

Temperature measurements are taken in living tissue of the host organism and correlating the temperature readings to the low frequency magnetic field causing alteration in dielectric properties and/or conductivity and/or frequency dependent dispersion curves. Once the temperature is correlated with these measurements, (dielectric properties, conductivity and frequency dependent dispersion curves) these measurements are then made along three axes at right angles to one another in the host organism from which a three dimensional temperature map of the body is produced by restructuring them in a three dimensional temperature model by computer processes well known in the art.

The frequency of the magnetic field is selected to enhance the dielectric properties, conductivity and electric dipoles of the neuronal cells and will vary depending upon the particles employed therein. The frequency, however, is adjusted so that thermal effects thereby obtained are not due to hysteresis loss from the particles themselves but rather the alteration in conductibility, dielectric properties and electric dipoles of the neuronal cells that are brought about by the use of the particles of the present invention. Generally, the range of frequencies that may be employed will be anywhere from about 1 Hz to about 500 MHz; 1 Hz to about 100 MHz; 1 Hz to less than 13 MHz; 1 Hz to about 100 KHz; 1 hertz up to less than 50 kilohertz and especially from about 10 hertz up to about less than 50 kilohertz as well as any frequency within these ranges or range of frequencies within the aforesaid ranges.

The present invention, therefore, will be practiced at the above frequencies and the copending applications incorporated herein by reference will give the person of ordinary skill in the art a disclosure of how to practice the present invention with the exception that the frequencies described above will be employed in lieu of those utilized in such copending applications.

To further illustrate the operation of this instant invention, the following treatment scenario is provided.

Reference herein to tissue, organ or cell population is intended in its most embracive and comprehensive sense, referring in general to the region of the host organism affected by the invasive abnormality, or the treatment region, as the context requires.

The subject receives an intravenous injection or direct injection of a colloidally suspended particle such as iron porphyrin (FeTPPS$_4$) at a dosage of 2–10 mg/kg. After a prescribed period of time which is dependent on the method of introduction of the particles i.e. after 24 hours–14 days after intravenous injection and 20 hours–10 days after direct injection, the subject is exposed to an alternating electromagnetic field at a frequency of 1 Hz to 100 MHz in thise case 500 Hz for a period of approximately 10–20 minutes. The alternating electromagnetic field may be applied via a coil arrangement or via capacitor plates or via electrodes in the tissue or any suitable means available in the state of the art, and consistent in application to this present invention. The process may be repeated as is necessary.

This field supplies energy to the interior of the neuronal cells thereby affecting only the reactive and/or diseased neuronal cells and not the normal neuronal cells. The amount of energy can be precisely controlled to affect only the reactive and/or diseased neuronal cells and not the normal neuronal cells.

In summary, the introduction and absorption of minute particles into the neuronal cells alters the intracellular environment and the charge accumulation on the membrane. Consequently, lower power levels may be used to transmit energy into the neuronal cells. Lower frequencies may be used because of the alteration in membrane events and the effect on normal cells is greatly reduced because of the above as well as the state of the neuronal cell's membrane. In addition, modification can be performed by using particles to alter the extracellular environment as well. Ultrasound techniques are also enhanced.

In addition, since radio frequency fields can affect particles by causing reversible or irreversible changes in the particles, i.e. magnetostrictive induced vibrations, by affecting the particles with an alternating electromagnetic field in the range 1 Hz to 500 MHz either prior to or during treatment, the particles can be made more or less responsive to the field. This alternating field can produce acoustic changes in the particle and affect the neuronal cell and subcellular structures. Ultrasound can be used.

As disclosed by the applicant in his U.S. Pat. No. 4,136,683 and as disclosed in copending and commonly assigned application Ser. No. 535,390, Now U.S. Pat. No. 4,662,359, to application Ser. No. 422,941) of the same inventor and incorporated herein by reference, this present invention can be used to create a three-dimensional temperature map of the body. In addition, measurements of these properties in the manner described herein, allows one to follow the distribution of the particles in the body by following the change in the dielectric properties, conductivity, and frequency dispersion curves both before and after ingestion of the particles.

Molecules in a neuronal cell can be affected if $\mu B > kT$ (where $\mu$ is dipole moment, B is the field strength, k is the Boltzman constant, and T is absolute temperature). Consequently by introducing the particles and increasing the relative dipole moment in the neuronal cell the direct effects on molecules in the neuronal cell can be enhanced even beyond thermal effects. Therefore, this present invention may directly affect the molecules in the neuronal cell.

Through these processes the dielectric properties across the membrane can be affected including the stimulation and/or alteration of nerve impulses and/or electrical events.

The ionic environment around the surface of the particle by becoming polarized can produce increased dielectric properties as well. In addition, membrane effects with the anionic proteinaceious material which accumulates around the neuronal cells can produce local effects.

When you have a mixture with different dielectric properties relaxation phenomenon will occur not at a single frequency, but over a wide range of frequencies. The curve is broadened due to interactions in the mixture. Inclusion of material of low dielectric constant will lower the dielectric constant of the mixture. Therefore, the addition of particles to the inside of the neuronal cell broadens the frequency response of intracellular structures as compared to the other cells and structures. Particle geometry also affects the frequency response. Consequently, the presence of the particles allows for a differential affect on subcellular structures.

Through the use of magnetic susceptibility measurements as described in the applicant's U.S. Pat. No. 4,136,683 and as disclosed in copending and commonly assigned application Ser. No. 535,390, now U.S. Pat. No. 4,662,359, to application Ser. No. 522,941) and as disclosed in copending and commonly assigned application Ser. No. 627,536 of the same inventor and incorporated herein by reference, the uptake of particles in the neuronal cells and glial cells can be followed as a function of time. This may be used diagnostically to evaluate which neurons are affected by the disease process and by analyzing which cells take up the particles. The magnetic characteristics of the particle in the neuronal cell can be used to help diagnose which disease process is present in the neurological tissue. Magnetic mapping techniques can also be used.

The process of this present invention is further illustrated by the following examples:

EXAMPLE I

A colloidal solution of $Fe_3O_4$-dextran-transferring is prepared in a concentration of 20 mg/cc in Rogers lactate. An intravenous injection of 2 cc is performed slowly over a period of 5 minutes. Over the next 48–72 hours, periodic measurements of magnetic susceptibility using a SQUID magnetometer as well as magnetic mapping measurements are performed. This allows identification of the neuronal cells which are involved, as well as helping to determine the type of disease process and the point in time of maximum uptake of the particles. At this time, the subject is subjected to the alternating electromagnetic field which destroys the reactive and/or inflammatory diseased cells in the tissue. Any diseased neurological tissue in the body can be treated by this process.

EXAMPLE II $FeTPPS_4$-Chloride 20 mg/cc is injected into the cerebrospinal fluid. After 26 hours localization is achieved in the neurons and the area to be treated is placed in a helical coil where an alternating electromagnetic field is applied. The field is applied for 3–4 minutes to achieve the alteration in cellular behavior and th disease process modified.

EXAMPLE III

A colloidal solution of $Fe_3O_4$-dextran-transferrin is prepared in a concentration of 20 mg/cc in Ringers lactate. 1 cc is injected stereotactically into the nigrostriatal pathway. After 24 hours localization is achieved in the thalamus. An alternating electromagnetic field is then applied to modulate thalamic function.

EXAMPLE IV

A colloidal solution of $Fe_3O_4$-dextran-transferrin is prepared at a concentration of 20 mg/cc and 1 cc is injected into a myelinated nerve. Interaction occurs between the particles and the myelin after 72 hours. An alternating electromagnetic field is then applied to affect the myelin of the nerve as well as the conduction system within the nerve.

What is claimed is:

1. A process for the treatment of neurological or neuromuscular diseases and development without substantially damaging normal neuronal and supporting glial cells comprising:
   introducing to the neurological or neuromuscular tissue minute particles capable of being taken up by neuronal or glial cells, and allowing said introduced minutes particles to effect at least one event comprising intracellular events or membrane events in said neuronal or glial cells, and
   subjecting said neurological or neuromuscular tissue to a relatively low frequency electromagnetic field to selectively provide energy to said neuronal or glial cells to alter their function.

2. The process of claim 1 including, inducing magnetic or electric dipoles in said tissue or said cells.

3. The process of claim 1 including, introducing magnetic or electric dipoles into said tissue or said cells.

4. The process of claim 1 including,
   applying to said tissue a static magnetic or electric field.

5. The process of claim 1 including,
   said applying including said static magnetic or electric field being between 100 gauss and 80 kilogauss.

6. The process of claim 1 including,
   said subjecting step commencing generally after the completion of said introducing step.

7. The process of claim 1 including,
   said subjecting including said electromagnetic field being a relatively low frequency alternating electromagnetic field.

8. The process of claim 1 including,
   said subjecting including said electromagnetic field being a relatively low frequency oscillating electromagnetic field.

9. The process of claim 1 including,
   said subjecting including said electromagnetic field being a relatively low frequency pulsed electromagnetic field.

10. The process of claim 1 including,
    said subjecting including said electromagnetic field being between 1 Hz and about 100 MHz.

11. The process of claim 1 including,
    said subjecting including exciting said particles and raising the energy level of said tissue to destroy said cells or modify their behavior to decrease the degenerative process.

12. The process of claim 1 including,
    continuing said subjecting until an increase of intracellular temperature of between 8 and 100 degrees Centigrade is attained to modify, alter or kill disceased cells of said tissue.

13. The process of claim 1 including, introducing particles into the extracellular environment of said tissue to alter membrane events and potentiate energy delivery to diseased inflammatory or reactive cells or reduce energy delivery to normal cells.

14. The process of claim 1 including,
said introducing including introducing said particles intravenously, intra-arterially, intra-lymphatically or locally into cerebrospinal fluid for ultimate delivery to reactive or inflammatory diseased cells.

15. The process of claim 1 including,
selecting said particles to enhance the effect of ultrasound on said tissues and said cells, and
thereafter, subjecting said particles to ultrasound.

16. The process of claim 1 including,
producing an exciting alternating electromagnetic field by magnetostrictive induced vibrations, and
applying to said tissue and said cells said exciting alternating electromagnetic field.

17. The process of claim 16 including,
said subjecting including said field being an alternating electromagnetic field between 1 Hz and 500 MHz to affect said particles and make them more or less responsive to said exciting alternating electromagnetic field.

18. The process of claim 16 including,
affecting said particles to make them more or less responsive to said exciting alternating electromagnetic field.

19. The process of claim 16 including,
selecting said particles to include compositions that specifically affect intracellular and extracellular events in said tissue and cells.

20. The process of claim 1 including,
selecting said particles to include compositions that specifically affect intracellular and extracellular events in said tissue and cells.

21. The process of claim 1 including,
affecting said particles to make them more or less responsive to an exciting alternating electromagnetic field produced by magnetostrictive induced vibrations.

22. The process of claim 1 including,
applying an alternating electromagnetic field of said particles to produce acoustic changes in said particles and affect the cellular and subcellular structures of said tissues or cells.

23. The process of claim 1 including,
selecting said particles to acoustically affect intracellular and extracellular events in said tissue and cells or said particles and to affect the cellular and subcellular structures of said tissue and cells.

24. The process of claim 1 including,
modifying the function of neural cells, glial cells, nerves to neuromuscular structures.

25. The process of claim 1 including,
modulating the function of neural cells, glial cells, nerves or neuromuscular structures.

26. The process of claim 1 including,
modifying conduction in central and peripheral nerves and tracts in the central nervous system.

27. The process of claim 1 including,
choosing said particles in their size, shape, composition and conformation to be transported along a specific path or tract to a specific destination to modulate activity at the destination.

28. The process of claim 1 including,
choosing said particles in their size, shape, composition and conformation to be transported along a specific path or tract and modulate or affect activity in that path or tract including conductiion mechanisms.

29. The process of claim 1 including,
obtaining control of neurological, neuromuscular and other tissue during developmental phases and formation to help control development and function of the tissue.

30. The process of claim 1 including,
obtaining control to modulate and affect the conduction of nerve impulses.

31. The process of claim 1 including,
achieving modulation or control of the release of neurotransmitters at synapses or neuromuscular junctions.

32. The process of claim 1 including,
choosing said particles in their size, shape, conformation and composition to be taken up by subcellular components such as the mitochondria.

33. The process of claim 31 including,
controlling the metabolism in said cells.

34. The process of claim 1 including,
designing said particles to interact with the cell membrane or receptors to modulate and control conduction in the nerve and other cellular events.

35. The process of claim 1 including,
using chloroquin ammonium chloride, methylamine or similar agents to decrease uptake of said particles in certain cells to potentiate the effect in the remaining cells.

36. The process of claim 1 including,
choosing said particles in their composition, conformation, size and shape to produce an affect in a specific pathway as in myelinated versus unmyelinated.

37. The process of claim 1 including,
choosing said particles in their composition, conformation, size and shape to interact with the myelin layer in nerves and therefore modify nerve conduction.

38. The process of claim 1 including, choosing said particles in their composition, conformation, size and shape to interact with the myelin layer in nerves and affect myelin related diseases, i.e., the demyelinating diseases.

39. The process of claim 1 including, choosing said particles so that they are adapted to be, after said introducing step, taken up by glial cells, i.e. oligodendrocytes, and used to affect the function of the supporting cells and their interaction with neuronal cells.

40. The process of claim 1 including, choosing said particles to interact with the neuromuscular junction and thereby control and modulate neuromuscular activity.

41. The process of claim 1 including, choosing said particles in their size, shape, conformation and composition to be taken up by the unmyelinated pathways and to affect those pathways and their ultimate destination.

42. The process of claim 1 including, achieving control and modulation of the visual pathway or retinal ganglion cells.

43. The process of claim 1 including, using the differential in the rate of transport in different pathways of said particles to selectively affect one pathway or destination prior to, simultaneously with, or after another pathway or destination.

44. The process of claim 1 including,
said introducing including introducing said particles intravenously, intra-arterially or intra-lymphatically.

45. The process of claim 1 including,
said introducing including introducing said particles into the cerebrosphinal fluid.

46. The process of claim 1 including,
said introducing including introducing said particles directly into said tissue.

47. The process of claim 1 including,
said particles being ferromagnetic, paramagnetic or diamagnetic.

48. The process of claim 1 including,
said particles being colloidally suspended and under one micron in size.

49. The process of claim 1 including,
selecting said particles from the group comprising ferromagnetic, paramagnetic, and diamagnetic elements, inorganic compounds, organic compounds and combinations thereof, metalloporphyrins, $Fe_2O_3$, FeOOH, and metalloporphyrins.

50. The process of claim 1 including,
selecting said particles from the group comprising ferromagnetic, paramagnetic, and diamagnetic elements, inorganic compounds, organic compounds and combinations or complexes thereof, metalloporphyrins, $Fe_2O_3$, FeOOH, and metalloporphyrins.

51. The process of claim 50 including,
selecting said particles from the group comprising:
(a) cobalt, zinc, iron, chromium, nickel, platinum, rare earth metals such as dysprosium, erbium, europium, gadolinium, holmium, samarium, terbium, thulium, ytterbium, yttrium, and compounds thereof comprising dysprosium sulfate, erbium sulfate, europium oxide, europium sulfate, gadolinium oxide, gadolinium sulfate, holmium oxide, samarium sulfate, terbium sulfate, thulium oxide, ytterbium sulfide, yttrium oxide, yttrium sulfate, yttrium ferrioxide ($Y_3Fe_5O_{12}$), yttrium oxide ($Y_3Al_5O_{12}$), dysprosium-nickel, dysprosium-cobalt, gadolinium-iron, ytterbium-iron, cobalt-samarium, gadolinium-ytterbium, dysprosium-gallium, and actinide series elements and compounds thereof;
and combinations thereof.

52. The process of claim 50 including,
selecting said organic compounds from the group comprising:
(a) dextran metal complexes wherein said metal is selected from the group comprising cobalt, zinc, chromium, iron, gallium, manganese, nickel, platinum, dysprosium, erbium, europium, gadolinium, holmium, samarium, terbium, thulium, ytterbium, yttrium, dysprosium-nickel, dysprosium-cobalt, gadolinium-iron, ytterbium-iron, cobalt-samarium, gadolinium-yttrium, and dysprosium-gallium, and iron such as $Fe_2O_3$ particles, $Fe_3O_4$ particles and FeOOH particles and $Fe_2O_3$-dextran complexes, $Fe_3O_4$-dextran complexes, and FeOOH-dextran complexes,
(b) iron transporting and chelating compounds comprising ferric ammonium citrate, enterochelin, transferrin, metallothionein, hydroxamates, phenolates, ferrichromes, desferriferrichromes, ferritin, ferric mycobactins and iron sulfur proteins comprising ferredoxin and rubredoxin,
(c) porphyrins comprisng etioporphyrins, meso-porphyrins, uroporphyrins, coproporphyrins, protoporphyrins, dicarboxylic acid containing porphyrins, substituted prophyrins comprising tetraphenylporphyrin sulfonate and protoporphyrin containing molecules comprising hematoporphyrins, chlorophylls, and cytochromes,
and combinations thereof.

53. The process of claim 52 including,
substituting the natural occurring metal moiety of said porphyrin with a metal selected from the group comprising cobalt, zinc, chromium, gallium, iron, manganese, nickel, platinum, dysprosium, erbium, europium, gadolinium, holmium, samarium, terbium, thulium, ytterbium, yttrium, dysprosium-nickel, dysprosium-cobalt, gadolinium-iron, ytterbium-iron, cobalt-samarium, gadolinium-yttrium, and dysprosium-gallium,
and combinations thereof.

54. The process of claims 52 or 53 including,
said iron transporting, iron chelating and porphyrin compounds being chemically complexed with dextran.

55. The process of claim 54 including,
said composition being chemically complexed with an antibody.

56. The process of claim 52 including,
selecting said metal-organic compound complexes from the group comprising Fe(III) Tetraphenylporphyrin sulfonate (TPPS4) Acetate, Fe(III) TPPS4 Acetate 4Na Salt ($H_2O$), Fe(III) Mesoporphyrin IX Chloride, Fe(III) TPPS4chloride, Co TPPS4, Co(III) MesoTPPS4 Tetra Na Salt (Acetate), Fe Phthalocyanine Tetrasulfonate, Tetra sodium salt, Tetra Sodium-meso-Tetra (4-sulfonate-phenyl) Porphine (12 hydrate), Fe(III) Tetra (N-Methyl 4-Puridyl) Porphyrin Pentachloride, Fe Phthalocyanine, Hemin, Fe-Hematoporphyrin D (HPD), Fe-Acetoxyethyl vinyl Deuteroporphyrin, Fe-Protoporphyrin IX, Fe-Deuteroporphyrin 2, 4 bis acetal, Mn-TPPS4, CO-N+MTPyP, Mn-N+MTPyP, Co-Mesoporphyrin X, Protochemin, Deuterchemin, Meso-tetra (4-N methyl pyridyl)hemin tetraiodide, Meso-tetra (4-carboxy phenyl)hemin, Ni-TPPS, Ni-HPD, Mn-mesoporphyrin IX, Co-Protoporphyrin IX, Mn-Protoporphyrin IX, Sn-Protoporphyrin IX, Co-HPD, Mn-HPD, Gd-TPPS, Gd-HPD, Hematoporphyrin Mono-acetate-Fe, Ferretin-Fe, Ferredoxin-Fe(4), Transferrin-Fe, Hematoporphyrin Diacetate-Gd, GdFe-TPPS4, GdFe2-HPD, FeTPPS4$(OH_2)_2$ $ClO_4$-, FeTPP $(OH_2)_2$ $ClO_4$-, Fe-Nitrolacetate, Fetetransulfinated phalocyanine, Bisimidazole (FeTPPS) $ClO_4$-, Rubrium-ferricytochrome/C,
and combinations thereof.

57. The process of claim 56 including,
said metal-organic compound complexes being chemically complexed with dextran.

58. The process of claim 57 including,
said composition being chemically complexed with an antibody.

59. The process of claim 1 including,
using magnetic or electric dipoles already present in said tissues or said cells.

60. The process of claim 1 including, said subjecting including said electromagnetic field activating magnetic or electric dipoles present in said tissues or said cells.

61. A process for the treatment of neurological or neuromuscular diseases and development without substantially damaging normal neuronal and supporting glial cells comprising:

introducing to the neurological or neuromuscular tissue minute particles capable of being taken up by neuronal or glial cells, and allowing said introduced minute particles to effect at least one event comprising intracellular events or membrane events in said neuronal or glial cells, and subjecting said neurological or neuromuscular tissue to a relatively low frequency electromagnetic field to activate magnetic or electric dipoles present in said tissue or said cells.

* * * * *